(12) United States Patent
Ørum et al.

(10) Patent No.: US 7,682,786 B1
(45) Date of Patent: Mar. 23, 2010

(54) MODULATION OF THE BINDING PROPERTIES OF NUCLEIC ACID BINDING PARTNERS

(76) Inventors: Henrik Ørum, Vildrosevej 3, DK-3500 Vorlose (DK); Ane-Ullerup Lester, Skyttedal 20, DK-2850 Narum (DK)

( * ) Notice: Subject to any disclaimer, the term of this patent is extended or adjusted under 35 U.S.C. 154(b) by 833 days.

(21) Appl. No.: 08/894,813

(22) PCT Filed: Mar. 4, 1996

(86) PCT No.: PCT/EP96/00892

§ 371 (c)(1),
(2), (4) Date: Dec. 7, 1997

(87) PCT Pub. No.: WO96/27679

PCT Pub. Date: Sep. 12, 1996

(30) Foreign Application Priority Data

Mar. 4, 1995 (EP) ................... 95103122
Nov. 30, 1995 (EP) ................... 95118843

(51) Int. Cl.
*C12Q 1/68* (2006.01)
(52) U.S. Cl. ......................................................... 435/6
(58) Field of Classification Search .................. 435/6, 435/91.2, 40.3, 40.51, 40.52, 810; 536/23.1, 536/23.2, 23.7, 24.1, 24.3, 24.31, 24.32, 536/24.35; 204/427
See application file for complete search history.

(56) References Cited

U.S. PATENT DOCUMENTS

| 5,599,667 | A | * | 2/1997 | Arnold, Jr. et al. | ............. | 435/6 |
| 5,747,254 | A | * | 5/1998 | Pontius | ......................... | 435/6 |
| 5,861,250 | A | | 1/1999 | Stanley et al. | | |

FOREIGN PATENT DOCUMENTS

| EP | 0 229 442 | | 7/1987 |
| EP | 0 318 245 | | 5/1989 |
| WO | WO 91/02088 | | 2/1991 |
| WO | WO 91/06679 | | 5/1991 |
| WO | WO 92/20703 | * | 11/1992 |
| WO | WO 93/24652 | * | 12/1993 |
| WO | WO 95/00666 | | 1/1995 |

OTHER PUBLICATIONS

Nielsen et al, "Sequence specific inhibition of DNA restriction enzyme cleavage by PNA", Nucleic Acids Res. 21(2):197-200, 1993.*
Stratagene catalog, p. 39, 1988.*
Nielsen et al, Nuc. Acids Res. (1993) 21:197-200.*
Pontius et al, Proc. Natl. Acad. Sci. USA, vol. 88, pp. 8237-8241, Sep. 1991, "Rapid renaturation of complementary DNA strands mediated by cationic detergents: A role for high-probability binding . . . ".
Ørum et al, Nucleic Acids Research, 1993, vol. 21, No. 23, pp. 5332-5336, "Single base pair mutation analysis by PNA directed PCR clamping".
Cotton, 10222 Mutation Research, 285 (1993), "Current methods of mutation detection".
Noble et al., Drug Development Research, 34: 184-195 (1995), "Impact of Biophysical Parameter on the Biological Assessment of Peptide Nucleic Acids, Antisense Inhibitors of Gene Expression".
Pitha, Advances in Polymer Science 50, 1983, "Physiological Activities of Synthetic Analogs of Polynucleotides".
Buttrey et al., Tetrahedron, vol. 31, p. 73 to 75, Synthetic Analogues of Polynucleotides-XIII.
Uhlmann et al, Methods in Molecular Biology, vol. 20, 1993, "Oligonucleotide Analogs Containing Dephospho-Internucleoside Linkages".
De Koning et al, 90(1971) Recueil, "Unconventional Nucleotide Analogues. VI.".
Stirchak et al, Nucleic Acids Research, vol. 17, No. 15, 1989, "Unchanged stereoregular nucleic acid analogs: 2. Morpholino nucleoside oligomers with carbamate internucleoside linkages".
"*Synthetic Analogs of Nucleic Acids*", by Josef Pitha, Mitsuru Akashi, Marcin Draminski; Biomedical Polymers Polymeric Materials and Pharmaceuticals for Biomedical Use; edited by Eugene P. Goldberg and Akio Nakaima (1980) pp. 271-297.
David R. Corey, "Peptide nucleic acids: expanding the scope of nucleic acid recognition," TIBTECH, 15: 224-229 (1997).
Hyrup et al., "Peptide Nucleic Acids (PNA): Synthesis, Properties and Potential Applications," Bioorganic & Medical Chemistry, 4: 5-23 (1996).

\* cited by examiner

*Primary Examiner*—Kenneth R. Horlick
(74) *Attorney, Agent, or Firm*—Carpenter Patent Law; Robert K. Carpenter

(57) ABSTRACT

A method for specifically determining the presence of a target by contacting said target in the presence of other targets with a probe capable of binding to said target to form a complex of said target with said probe, wherein the contacting is performed in the presence of a compound enhancing the specificity of said binding or the complex formed is contacted with a compound enhancing the specificity of said binding. This method opens the way to a better discrimination between related nucleic acid sequences in diagnostic assays.

11 Claims, 7 Drawing Sheets

Figure 2

A: Matched PNA/DNA duplex

| Reaction: | 6 | 4 | 1 | 3 |
|---|---|---|---|---|
| Initial SDS concentration (added before hybridisation) | 1.0% | 0.1% | 0% | 1.0% |
| Final SDS concentration (added after hybridisation) | 0.1% | 0.1% | 1.0% | 1.0% |
| Thermostability in oC | 69.2°C | 69.0°C | 56.2°C | 57.0°C |

B: Mismatched PNA/DNA duplex

| Reaction: | 7 | 2 | 5 |
|---|---|---|---|
| Initial SDS concentration (added before hybridisation) | 1.0% | 0% | 0.1% |
| Final SDS concentration (added after hybridisation) | 0.1% | 0.1% | 0.1% |
| Thermostability in oC | 40.8°C | 40.0°C | 40.6°C |

MODULATION OF THE BINDING PROPERTIES OF NUCLEIC ACID BINDING PARTNERS

The present invention is directed to a method for specifically determining the presence of a nucleic acid or a non-natural nucleic acid binding partner by binding to a nucleic acid or another non-natural nucleic acid binding partner, a method for the detection of a nucleic acid or a non-natural nucleic acid binding partner, a method for discriminating nucleic acids as well as compositions prepared in these methods and useful for these methods.

Underlying all DNA diagnostic methods is the unique ability of complementary nucleic acids to undergo reversible denaturation. Thus, when a DNA probe is mixed with a complex mixture of nucleic acids under appropriate conditions it will seek out and bind only to its complementary target sequence. Two important parameters which are used to describe the suitability of a diagnostic probe are affinity and specificity. Affinity is a measure of the binding strength of the probe to its target sequence and specificity is a measure of its ability to discriminate between a fully complementary and a mismatched target sequence. In practise, the use of highly specific probes minimizes the risk of obtaining false positives whereas the use of high affinity probes maximizes sensitivity as it allows the probe/target complex to survive lengthy procedures.

Up to now many proposals for nucleic acid analogues or non-natural nucleic acid binding partners (NNNBPs) have been made. However, only the so called peptide nucleic acids (PNAs, WO 92/20703) have been shown to be of value for both therapeutic and diagnostic use. Compared to standard nucleic acids PNA exhibits both increased affinity and specificity for its target nucleic acid. Hence, PNA is superior compared to DNA as a diagnostic probe.

The present invention describes that the specificity of PNAs can be increased even further by adding certain ingredients to the reaction mixture, hence further increasing the usefulness of PNAs in diagnostic assays.

In Biomedical Polymers (1980), edited by Eugene P. Goldberg and Akio Nakaima, pages 271-297, there is disclosure that sodium dodecylsulphate (SDS) can intercalate into vinyl analogs of polynucleotides and that this intercalation confers upon the vinyl analogue an electronegative charge which considerably reduces its ability to bind (affinity) to polyanions like nucleic acids.

It is an object of the present invention to improve nucleic acid assays using NNNBPs in general and PNAs in particular.

Subject of the present invention is a method for specifically determining the presence of a particular target(s) by contacting said target(s) in the presence of target(s) not to be determined with a probe(s) capable of binding to said target(s) to form a complex of said target(s) with said probe(s) wherein
a) the contacting is performed in the presence of a compound enhancing the specificity of said binding, or
b) the complex formed is contacted with a compound enhancing the specificity of said binding.

A further object of the present invention are reagents for conducting said binding and uses of compounds enhancing the specificity of said binding.

Target(s) and probe(s) are able to bind to each other by base pairing and are either nucleic acids or non-natural nucleic acid binding partners (NNNBP). The combination of probe(s) and target(s) both being nucleic acids is excluded.

A nucleic acid in the present invention is a labelled or unlabelled deoxyribonucleic acid or a ribonucleic acid containing a backbone of sugar and phosphate moieties and the bases G, A, T, C, U and optionally modified bases bound to said backbone. It can be of any desired origin. It can be isolated from organisms or be present in organisms. Possible organisms include by example, but not by exclusion, viruses and bacteria, but also animal, plant, or human cells. The nucleic acid can be obtained in various ways, for example by extraction or concentration from organisms or be generated by for example amplification or cDNA formation. The nucleic acid can also be synthesized chemically. The nucleic acid can in the beginning of the method of the present invention be present as a double stranded or single stranded nucleic acid. Preferably it is single stranded or made single stranded by known methods, like denaturation by heat or by low ionic strength.

A backbone in either a nucleic acid or a NNNBP is a structure of at least two substantially identical units, each carrying a specific nucleobase. The naturally occurring backbone is the sugar phosphate backbone. This can be modified at the phosphate, Acc. Chem. Res. 1995, 28, 366-374, or at the sugar, Acc. Chem. Res. 1995, 28, 366-374, or more dramatic changes by using morpholino, Acc. Chem. Res. 1995, 28, 366-374, vinyl, Acc. Chem. Res, 1995, 28, 366-374 or pseudopeptide, Science 1991, 254, 1497-1500, moieties as the repeating units.

Targets not to be determined are especially nucleic acids which differ in base sequence from the target. In some cases below, target to be determined and target not to be determined are named related targets or nucleic acids. Targets not to be determined can e.g. be, in case of the determination of a nucleic acid indicating an illness or pathogen, a nucleic acid not occurring in healthy persons and being different in base sequence from the nucleic acid in the healthy state.

NNNBPs are non-naturally occurring molecules being able to bind to nucleic acids by base pairing. NNNBPs are further defined as being structurally different from nucleic acids in at least the backbone. The structural difference can result from the addition of moieties to the backbone which are preferably not naturally occurring or in replacement of one more or all components of the backbone, preferably the phosphate and/or the sugar moiety by other moieties. NNNBPs are defined according to the present invention to bind to a nucleic acid by (preferably specific) base pairing via hydrogen bonds between a base of a nucleic acid and a base of the NNNBP, thus forming a complex. Bases are naturally occurring nucleobases, like A, C, G, T and U, or heterocyclic bases not present in naturally occurring nucleic acids but being derived therefrom, e.g. by substitution of atoms, like substitution of O by S, NH or $CH_2$ or by addition of groups, e.g. derivisation of an atom for example participating or influencing the hydrogen bonding between the base of the NNNBP and the corresponding base of the nucleic acid or NNNBP. The most preferred complexes contain one strand of the NNNBP and one strand of a nucleic acid or two strands of the NNNBP and one strand of a nucleic acid. In the first case (preferred) the complex is called a duplex and in the second case the complex is called a triplex.

Therefore NNNBPs can be defined as having the general formula $$BB(-L)_n \qquad \text{(Formula 0)}$$

wherein BB is a backbone different from nucleic acids and

L is selected from the group of naturally occurring nucleobases or heterocyclic bases not present in naturally occurring nucleic acids.

n is a natural number between 2 and 100.

It must be understood that both BB and L can be unsubstituted or substituted by moieties not destroying the capability of the NNNBP to bind to its complementary nucleic acid. Especially, if the NNNBP is used as a probe, it may carry a label. Such probes can therefore be defined as compounds of the formula $$(BB(-L)_n)(label)_o \quad \text{(Formula 00)}$$

wherein BB, L and n are defined as above and label is a directly or indirectly detectable group or an immobilizable group and o is a natural number of one or more, preferably of between 1 and 5.

Preferably the NNNBPs have a higher affinity for their complementary nucleic acids compared to the analogous natural nucleic acid. Some NNNBPs are summarized in Recueil 91, 1069-1080 (1971), Methods in Molecular Biology 29, 355-389 (1993), Tetrahedron 31, 73-75 (1975), J. Org. Chem. 52, 4202-4206 (1987), Nucl. Acids Res. 17, 6129-6141 (1989), Unusual Properties of New Polymers (Springer Verlag 1983), 1-16, Specialty polymers (Springer Verlag 1981, 1-51, WO 92/20823, WO 94/06815, WO 86/05518 and WO 86/05519. These are peptide and non-peptide compounds. The NNNBP can be a charged or non-charged molecule. Preferred are NNNBPs carrying less charges than natural nucleic acids, most preferred are essentially uncharged NNNBPs. The most preferred NNNBPs do not contain a sugar/phosphate backbone, but contain a peptide backbone, e.g. as described in WO 92/20702 and WO 92/20703. Preferred NNNBPs are compounds comprising a polyamide backbone bearing a plurality of bases at spaced locations along said backbone, each base being bound to a nitrogen atom of said backbone, compounds capable of binding to a nucleic acid having a complementary base sequence to form a complex which is more stable against denaturation; e.g. by heat or low ionic strength, than a complex between a nucleic acid analogous to the NNNBP and its complementary nucleic acid. Especially preferred are compounds having the general formula

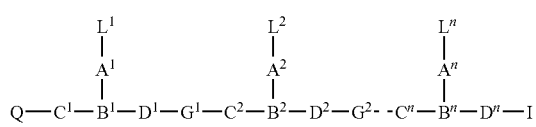

Formula 1 n is at least 2, each of $L^1$-$L^n$ is independently selected from the group consisting of hydrogen, hydroxy, ($C_1$-$C_4$)alkanoyl, naturally occurring nucleobases, non-naturally occurring nucleobases, aromatic moieties, DNA intercalators, nucleobase-binding groups, heterocyclic moieties, reporter ligands and chelating moieties;

each of $C^1$-$C^n$ is $(CR^6R^7)_y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, aralkyl, heteroaryl, hydroxy, ($C_1$-$C_6$)alkoxy, ($C_1$-$C_6$)alkylthio, $NR^3R^4$ and $SR^5$, where $R^3$ and $R^4$ are as defined below, and $R^5$ is hydrogen, ($C_1$-$C_6$)alkyl, hydroxy, alkoxy, or alkylthio-substituted ($C_1$ to $C_6$)alkyl or $R^6$ and $R^7$ taken together complete an alicyclic or heterocyclic system;

each of $D^1$-$D^n$ is $(CR^6R^7)_z$ (preferably $CR^6R^7$, $CHR^6CHR^7$ or $CH_2CR^6R^7$) where $R^6$ and $R^7$ are as defined above;

each of y and z is zero or an integer from 1 to 10, the sum y+z being at least 2, preferably greater than 2, but not more than 10;

each of $G^1$-$G^{n-1}$ is —$NR^3CO$—, —$NR^3C^5$—, —$NR^3SO$— or —$NR^3SO_2$—, in other orientation, where $R^3$ is as defined below;

each of $A^1$-$A^n$ and $B^1$-$B^n$ are selected such that:

(a) A is a group of formula (IIa), (IIb), (IIc) or (IId), and B is N or $R^3N^+$; or (b) A is a group of formula (IId) and B is CH;

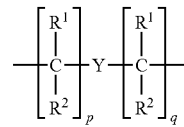

Formula IIa

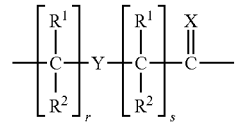

Formula IIb

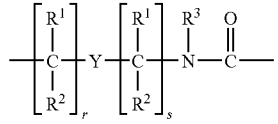

Formula IIc

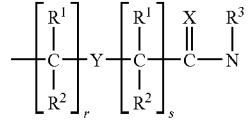

Formula IId wherein:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, ($C_1$-$C_4$)alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($C_1$-$C_4$)alkyl, hydroxy- or alkoxy- or alkylthio-substituted ($C_1$-$C_4$)alkyl, hydroxy, alkoxy, alkylthio and amino; and Q is —$CO_2H$, —CONR'R", —$SO_3H$ or —$SO_2$—NR'R" or an activated derivative of —$CO_2H$ or —$SO_3H$ and I is —NR'R" wherein R' and R" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers.

If not otherwise stated alkyl groups in other substituents (like alkoxy) contain preferably 1 to 4 carbon atoms and are preferably acyclic and unbranched. A reactive group according to the present invention is a group that can be used to attach a label or can be used to immobilize the probe or the target on a solid phase. Examples of such reactive groups are activated esters, like N-hydroxy-succinimide-esters. An amino protecting group is a group as generally used e.g. in peptide synthesis to protect amino groups from undesired reaction with other molecules. These protecting groups can be removed if desired by methods not destroying the attachment of the amino group to the main component of the molecule. Suitable protecting groups are N-Boc or similar.

Intercalators are molecules which can insert themselves between the bases in duplex DNA. Such intercalators generally are polyaromates like ethidiumbromide or acridinium compounds.

Chelators are molecules which are able to complex molecules or already contain such molecules complexed such that the complex is not unwantedly destroyed during the steps of the method according to the invention. Chelators can be used to label the probe or the target, e.g. by complexing a detectable metal ion like ruthenium or other fluorescent moieties. Especially suitable chelators contain ruthenium complexed by bipyridyl moieties.

Peptides can be useful as reporter ligands or can be used to attach labels to the probe. An especially suitable peptide is the kemptide moiety that can be used to attach a labelled phosphate group to the probe.

Proteins especially comprise biologically active proteins, e.g. proteins which can be recognized by other moieties. Such recognizable proteins are e.g. immunologically active proteins that can be recognized by antibodies. Further biologically active proteins are enzymes that can be used to convert substrates into products. Suitable enzymes are e.g. peroxidase or alkaline phosphatase.

Carbohydrates are sugar molecules which can be used to attach a probe to a detectable moiety or a solid phase. Some carbohydrates e.g. are recognized by binding partners, like sugars are recognized by lectins.

Steroids are especially useful to attach the probe to other moieties, like detectable moieties or solid phases. Especially suitable steroids are steroids not usually occurring in the sample.

Nucleosides are moieties containing a sugar moiety and a base moiety as usually occurring in natural nucleic acids.

Nucleotides are generally referred to as compounds being composed of at least one phosphate, one sugar and one base moiety as usually occurring in naturally occurring nucleic acids.

Oligonucleotides are generally referred to as nucleic acids having a lengths of between 2 and 50 nucleotide moieties.

Soluble polymers are e.g. polyethyleneglycols.

Non-soluble polymers are compounds useful for the immobilization of the probe. They comprise e.g. resins or polystyrol.

Preferably these NNNBPs have attached a group which acts as a label, a reporter group or a reactive group for binding of the NNNBP to solid phases. The group can be attached at the base moiety or at the backbone of the NNNBP. A modification at the base moiety can be at any site of the base. Modification of the backbone can be at any atom, but is preferably at one or both of the ends of said backbone.

A target to be determined according to the present invention is a molecule whose presence or amount in a sample is intended to be determined. In most cases the amount of target present in the sample will not be known. However, in some cases it may be that a method of the present invention will only have to determine whether a target is present or not. In this case it may be that the amount of target present is predefined. In the most important cases, however, the amount of target is unknown and undefined prior to the determination and is somehow correlated to the amount of a nucleic acid or a nucleic acid containing agent, like cells etc., in the sample.

In contrast thereto the probe is a means for determining a target. Therefore the presence and amount of probe in a reagent that is added to a sample will be defined and/or known. In most cases the amount of probe will exceed the amount expected to be present in the sample. Therefore the amount of binding of the probe to a corresponding target gives an estimation of the presence of a target in the sample. It is further preferred that the amount of probe not bound to the target after incubation is removed from the complex formed between target and probe.

The formation of the complex between the targets and the probe(s) can occur under conditions commonly applied to the hybridization of nucleic acids to form double stranded nucleic acid hybrids, but can also occur under low salt conditions. Such conditions are described in WO 92/20703. However, in the present invention it is preferred to use lower salt concentrations than usual. Preferred low salt concentrations are from 5 to 50 mM. Salts can be those commonly applied in hybridization reactions. They include for example sodium, potassium, magnesium or mangan as cations and phosphate, sulphate or chloride as anions. Most preferred are salts having buffer characteristic like sodium phosphate. The low salt concentrations are preferred, because it destabilizes nucleic acid/nucleic acid interactions that may compete with NNNBP binding to its complementary nucleic acid or NNNBP. Also, many immunological and enzymatic reactions are compatible with low salt conditions, hence allowing detection of the resulting complex without change of the reaction mixture. In order to use the invention in the most effective way, both the target(s) and the probe(s) and the compound are dissolved in solution during their incubation. However, it is possible to immobilize the complex formed on a solid phase after that incubation.

The core of the present invention is the use of a compound that enhances the specificity of the binding between the NNNBP and the nucleic acid and/or NNNBPs. Up to now no compounds have been found that allow the modulation of the binding specificity of nucleic acids to each other or to NNNBPs. Though some compounds used in the method of the present invention have been known for a long time, they have not been recognized as effective in enhancing the specificity of binding between nucleic acids and their binding partners. One of the compounds effective according to the present invention is sodium dodecylsulphate (SDS) which is commonly used to inhibit binding of nucleic acids to surfaces to which they have an affinity. Further it was concluded in the prior art that SDS would be even disadvantageous when used together with NNNBPs because the experiments performed in the art showed that the affinity of the NNNBPs used in the art to polyanions (nucleic acids are also polyanions) was decreased. Apparently the art was discouraged to use SDS in binding assays because it appears to bind to the NNNBP which binding creates a repulsion between the NNNBP and the polyanions. The present invention, however, has found, that for example SDS has the unexpected property to enhance the specificity of the binding of NNNBPs to nucleic acids or/and NNNBPs.

Further it was found that besides SDS a number of other compounds have the same characteristics. Preferred compounds have at least one hydrophobic part and at least one ionic or hydrophilic part and are selected from the group of surfactants or detergents. Surfactants are defined as compounds reducing the surface tension of aqueous solutions. Detergents are compounds comprising an ionic or hydrophilic part and a lipophilic part. Surfactants and detergents are compounds which tend to form micels in aqueous solutions. It is preferred that the above mentioned compounds are soluble in aqueous solutions, because nucleic acids and NNNBPs are also soluble in aqueous solutions. It was recognized according to the invention that compounds having an overall charge are preferred. Among these, compounds that have one or more negative charges are preferred over positively charged. Charged molecules are defined as molecules that are substantially dissociated from their counter ion when dissolved in water, less preferred are zwitter ionic compounds. The least preferred are uncharged compounds. Preferred compounds according to the present invention are sodium dodecylsulfate (SDS) or lithium dodecylsulfate (LiDS) and DTAB (dodecyl trimethyl ammonium bromide).

The concentration of the compounds required for enhancing the specificity could vary to some extend depending on the compound used.

For example, SDS is preferably used in concentrations ranging from 0.05 to 0.5% w/v, especially preferred concentrations are between 0.1 and 0.2% equivalent to molar concentrations of 1.73 mM to 17.34 mM and preferred 3.47 mM to 6.94 mM. As a general rule, the concentration of the compound should be in the upper part of the range when the salt concentration in the mixture is low and should be in the lower part of the range when the salt concentration is high or as usual in hybridization assays. Further it was observed that the lower the initial $T_M$ of the probe/target duplex, the less SDS is required to produce an effect. Consistent with this finding a line can be fitted to a plot of the initial $T_M$ of each PNA/DNA duplex versus the SDS concentration required to produce the effect according to the invention. Further it is preferred to use a concentration which is above a concentration needed for micellar formation. Further when binding PNAs to PNAs, slightly higher SDS concentrations may be needed than expected from the initial $T_M$ of these duplexes.

The compounds that enhance the specificity of binding of an NNNBP can be used to specifically determine nucleic acids or NNNBPs or even groups of nucleic acids or non-natural nucleic acids even in the presence of nucleic acids or non-natural nucleic acids which are not desired to bind to the NNNBP. Specificity in the definition of the present invention is defined as the ability to discriminate between nucleic acids or non-natural nucleic acids having different base sequences. The nucleic acids to be distinguished contain at least one different base in a given position (other nucleic acids) which means a base mismatch to the NNNBP. This position is located within the base positions of the NNNBP being bound to the nucleic acid or NNNBP by base pairing. Of course, the NNNBP can contain other parts which do not participate in binding to the nucleic acid.

The method of the invention can be conducted in several ways, depending on the kind of target and probe. In a first embodiment, which is preferred, a target is a nucleic acid and the probe is an NNNBP. This may be an embodiment which is especially suitable for determining a nucleic acid which is correlated to a specific infection or as an acquired or inherited genetic disease. In this case after providing a sample solution containing a target nucleic acid, the probe NNNBP is added to the sample solution. The formation of a complex between the nucleic acid and the NNNBP is taken as an indication of the presence or the amount of target nucleic acid in the sample. In this case in most determinations the amount of target nucleic acid is unknown before the determination. Therefore it may be advantageous to correlate the signal obtained by complex formation to the signal obtained by measuring the complex of a sample containing a known amount of this target nucleic acid and the probe NNNBP. Preferably this NNNBP is then either detectably labelled or labelled in such a way as to allow immobilization on solid supports (in this case a further detectably labelled probe may be required).

In another case both the target and the probe are NNNBPs. This may be a case wherein the presence, absence or amount of an analyte, especially a nucleic acid, was determined indirectly by the presence, absence or amount of a target NNNBP. Then the presence or amount of the target NNNBP is an indication of the presence or absence of the analyte in the sample. The second NNNBP (the probe) is used to determine the presence, absence or amount of the first NNNBP and therefore is an indication of the presence, absence or amount of the analyte in the sample. In this case the amount of the target NNNBP is defined by the amount of analyte in the sample. An example of such an embodiment is the determination of a nucleic acid by binding to the analyte nucleic acid or a part thereof the target NNNBP. In this case either the nucleic acid contained in the original sample or the target NNNBP can be discriminated from another nucleic acid or NNNBP in the solution according to the present invention. The probe NNNBP can also distinguish between the target NNNBP and other sequences in the sample solution, e.g. a nucleic acid not to be determined but having a similar base sequence. In this case the probe NNNBP is complementary in base sequence to the target NNNBP or a part thereof.

In a third embodiment, the target is NNNBP and the probe is a nucleic acid. This case is similar to the second embodiment but differing from that in that the probe is a nucleic acid and its binding to the target is used as an indication of binding the target NNNBP to an analyte to be determined.

Therefore in the embodiments of the present invention both direct and indirect determinations are possible.

It is an object of the invention to use the difference in complementarity of the probe(s) to the base sequence of the target compared to targets not to be determined. Examples of nucleic acids differing at least one base position are alleles, for example the wild type and the sickle cell alleles of the β-globin gene. The differences can occur by mutation, insertion and deletion. A further example of targets that can be discriminated according to the present invention are the different sequences of the p53 gene.

The method of the present invention can also be used to determine a group of targets. If a group of targets comprises at least one segment which is identical in sequence, this segment can be used to determine all targets of said group together, even if said targets comprise other sequences that differs substantially. For example a group of bacteria (e.g. the members of the genus *Salmonella*) has a stretch of evolutionary conserved bases in their nucleic acids which is identical, but differs from the sequences of other genera, like *Chlamydia*.

It is important to understand that with the present invention it is possible to distinguish between targets closely related in sequence. On the other side it is possible to determine a group of targets having different sequences if they share a common target domain for example evolutionary conserved sequences motifs. To distinguish between closely related targets a segment of said target is chosen in which it differs in sequence from a closely related sequence not to be determined. To distinguish the target to be detected from the other targets, a sequence of the probe must be chosen to be complementary to this segment of the target, but having a mismatch to the corresponding sequence of the target(s) not to be determined.

Further the probe can comprise in addition to a segment complementary to the target segment(s) one or more egment(s) which are not complementary to corresponding segments of the target(s). These segments can be e.g. base sequences suitable for recognition of other nucleic acids or NNNBPs. The position of the mismatch is chosen such that the segment of the probe binding to the target embraces this mismatch site. Preferably the mismatch will be in close to the center of the binding segment. Of course it is possible to distinguish also targets containing more than 1 difference in sequence from targets not to be determined.

According to the method of the present invention, the base sequence of the probe(s) is chosen to be perfectly complementary to the segment of the target to be determined which differs in sequence from the sequence of other targets which should not be determined. The length of the target and in consequence hereof the length of the probe is a further means for influencing the affinity and specificity of the binding. The shorter the binding segment sequence of the probe, the higher the intrinsic specificity, but the lower the affinity. In case of the peptide nucleic acids according to WO 92/20703 the length of the binding segment should be between 10 and 20 bases to have excellent affinity and specificity. Most preferably the length is between 12 and 17 bases.

One core of the invention is the finding that using the compounds one can increase the differences in melting temperatures ($\Delta T_m$) of complexes of the probe and complementary targets and complexes of probe and target(s) which contain at least one mismatched basepair. This has the consequence, that the discrimination between the related nucleic acids is much easier than without the compound.

The higher specificity of the binding imposed by the compound, however, has the further consequence, that the temperature of the reaction mixture during the binding reaction can be lower than in reaction mixture without the compound, without considerable loss of specificity. This has the very important consequence that an assay can be completed much faster in the presence of the compound than in its absence (the speed with which NNNBPs bind to complementary nucleic acids increases as the temperature decreases, with maximum rates observed between 15 to 25° C. below the temperature at which the complex melts). The ability to carry out highly specific assays at low temperature is further of importance for routine and automated diagnostic applications, where high temperatures are inconvenient.

According to the present invention it is possible to conduct the method in at least three ways. In a first embodiment the compound is contacted with the sample containing the target to be determined prior to the formation of the complex between the probe and the target. This can be made by adding first the compound and then the probe to the sample. Without the intention to be bound to the statement, it is assumed that the better matching complex with the probe is formed quicker and is, after its formation, more stable than the complexes formable and perhaps formed between the probe and the targets not to be determined.

In a second embodiment of the invention the compound is added to the reaction mixture after formation of the complex between the probe and the target to be determined and possibly the (related) target(s) not to be determined. Again without the intention to be bound to this theory it is assumed that the compounds act to selectively destabilize the complexes having more mismatches in their sequence, hence deminishing the number of unwanted complexes whilst leaving the desired complexes intact.

Of course it is possible to add the compound at all stages between the first and second embodiment. Then intermediate embodiments are created having, however, the same inventive effect.

After formation of the complex, the presence of the target to be determined can be analyzed by the presence of said complex. There are a great variety of possibilities for determining the presence of duplex or triplex structures known in the prior art for either nucleic acids or complexes containing nucleic acids and NNNBPs. All these methods can be applied analogously to the methods of the present invention.

One simple way to determine the presence of a complex between probe and a target is the photometric watch of the change in absorbance of a reaction mixture during the process of increasing or decreasing the temperature of the mixture. This is commonly known as the detection of a melting curve. The absorbance of the mixture changes significantly at the melting temperature ($T_m$) of the complex to be determined. The presence of the complex can therefore be determined by checking whether the absorbance changes at the expected melting temperature.

In the more modern assays, either the probe or the target to be determined is modified to include a label. Ways to label probes or targets are generally known to the man skilled in the art. Probes or targets can be labelled during their synthesis or in a step subsequent to their synthesis. If probes or targets are labelled during synthesis, it is wellknown to use monomer units that are already labelled or that contain a reactive group that can used for attachment of a label. The synthesis can be performed in either a strictly chemical way or by including enzymatic steps. For the synthesis of nucleic acids it is commonly acknowledged that the most convenient synthesis includes the use of activated monoribonucleoside monophosphates, like in the phosphotriester method. Any labels can be introduced during synthesis e.g. according to EP-B-0 135 587. If the probe is labelled enzymatically, possible ways of synthesis include nick-translation or methods according to EP-B-0 063 879. If the probe is labelled after synthesis, there are also several ways described. According to DE-A-2915082 reactive groups in the base moiety can be reacted with labelling moieties. A further method of labelling after synthesis is described in EP-B-0 173 251. The target to be determined can also be labelled in several ways, e.g. by chemical labelling as described above, incorporation of labelled moieties in an enzymatic reaction, e.g. by nick translation, by extension with labelled moieties, e.g. by extension with terminal transferase and labelled mononucleotides or by enzymatic incorporation of labelled monomers, e.g. labelled mononucleotides by DNA- or RNA-polymerases.

A label according to the present invention is a directly or indirectly detectable group. Directly detectable groups are e.g. radioactive (e.g. by incorporation of $^{32}P$), coloured or fluorescent groups or metal atoms. Indirectly detectable groups include e.g. immunologically or enzymatically active compounds such as antibodies, antigens, haptens, or enzymes. These are detected in a subsequent reaction or reaction sequence, for example with a labelled immunological binding partner such as an antigen or an antibody against the antigen or the hapten or with a suitable enzyme substrate. Particularly preferred are haptens like bromine, digoxigenin, digoxin or fluorescein. A further preferred indirectly detectable group is biotin.

A reporter group is an indirectly detectable group. A reactive group according to the present invention is a group that can be used to create a label or can be used to immobilize the probe or the target on a solid phase. Examples of such reactive groups are activated esters, like N-hydroxy-succinimide-esters.

The label can be attached at any position in the probe or the target which does not prevent the probe from binding to the target. Preferred positions are the positions bearing heteroatoms like amino groups of the bases and reactive groups at the backbone, especially at either end of the backbone. Groups of the backbone suitable for coupling to a label can be groups in the monomer units that are used for coupling two monomer units together. Suitable groups contain carboxylic acid or primary or secondary amino groups. The reactions for coupling the label to the specific positions depends on the specific groups used for coupling and are generally wellknown to a man skilled in the art either from nucleotide chemistry or from peptide chemistry.

The complex containing such a label is preferably detected after binding the complex to a solid phase and removing any unbound labelled compounds, for example an excess of labelled probe. This binding can easily be made by using a so called capture probe, which hybridizes to a different segment of the target to be determined than the probe. Such a format is described, for example, in EP-A-0 079 139. Of course, this format can be modified such that the probe is bound to a solid phase rather than detectably labelled, so that the complex formed is bound to a solid phase after formation. Thereafter the immobilized complex can be detected by hybridizing to another segment of the target a detectably labelled probe and measuring the immobilized label.

However, even simple procedures, like Southern blots, dot blots as described in Method in Enzymunonology 100, 266-285 (1983) or reverse dot blot (as described in EP-B-0 237 362) can be applied. In the later case, the target to be determined is a nucleic acid generated from an amplification reaction using an original nucleic acid as a template in which a labelled moiety is incorporated during the amplification. The NNNBP is bound to a solid phase. After formation of the complex of the immobilized NNNBP and the detectably labelled target nucleic acid the amount of label attached to the solid phase is determined and used to calculate the amount of target nucleic acid originally present in the sample. The present invention is especially advantageous for the parallel hybridization of nucleic acids to a large number of spots of NNNBPs with different sequences. Such embodiments can be realized analogously to the embodiments described in WO 89/10977, WO 90/15070 and U.S. Pat. No. 5,202,231, using NNNBPs instead of oligonucleotides.

The present invention can be used to detect very easily nucleic acids which are a result of an amplification procedure like the extentions products (amplificates) described in EP-A-0 201 184.

The present invention has the advantage, that it can be used to enhance the sensitivity in diagnostic assays and to avoid stringency washes to dehybridize complexes containing targets which are not perfectly matching the probe and which are not to be determined.

A further object of the present invention is a reagent for conducting the binding of a nucleic acid or a non-natural nucleic acid to a non-natural nucleic acid binding partner wherein the reagent contains the non-natural nucleic acid binding partner and a compound enhancing the specificity of said binding and said compound is not sodium dodecyl sulphate. This reagent can in addition contain for example salts, buffer substances, as well as other adjuvants.

Further object of the present invention is a reagent kit for conducting the binding of a nucleic acid or a non-natural nucleic acid to a non-natural nucleic acid binding partner wherein the reagent kit contains in separate containers the non-natural nucleic acid binding partner and a compound enhancing the specificity of said binding, said compound not being sodium dodecyl sulphate. Again any of these containers can contain in addition for example salts, buffers and adjuvants.

BRIEF DESCRIPTION OF THE DRAWINGS

FIG. 2 shows the thermostability of matching versus mismatching PNA/DNA-complexes. It becomes clear that at constant SDS concentrations the order of complex formation and SDS-addition has very little influence on the thermostability.

The following examples shall describe the invention in more detail.

General Remarks

The PNA molecules used in the examples as NNNBPs can be prepared following the instructions in WO 92/20702 or can be purchased in monomer or oligomer form from PerSeptive Biosystems, Inc. Cambridge, Mass. 02139, USA. The DNA molecules were chemically synthesized oligonucleotides.

In each of the below mentioned reactions, if not otherwise stated, the binding reaction was conducted with the DNA-oligodeoxyribonucleotide 5'-TAGTTGTGACGTACA-3'

(SEQ.ID.NO. 6) as the nucleic acid. The reactions differ by the use of different NNNBPs (containing no or one or more mismatches).

EXAMPLE 1

SDS can be Used to Modulate the Affinity of PNA for its Complementary DNA

A series of 1 ml hybridisation reactions were set up containing 25 mM $Na_2HPO_4$, pH 7.0, 4.5 mM of PNA, 4.5 mM of complementary DNA oligonucleotide and SDS from 0 to 0.5%. The solutions were heated to 95° C. and left to form hybrids at room temperature over night. The following day additional 2 ml of the appropriate buffer (25 ml $Na_2HPO_4$, pH 7.0 and SDS from 0 to 0.5%) was added to the hybridization solutions and the thermal stability of each of the duplexes, measured as melting temperature, $T_m$, were determined spectrophotometrically using a Perkin-Elmer, λ2 spectrophotometer. A total of three different 15mer PNAs, a 18mer PNA and a control 15mer DNA were analyzed. As shown in figure the DNA/DNA duplex remains unaffected by SDS over the entire concentration range tested. In contrast, a rather sharp decrease in $T_m$ is observed with all PNA/DNA duplexes when the SDS concentration exceed a certain threshold. This result shows that SDS can be used to modulate the affinity of PNA for its complementary DNA.

Figure 1:
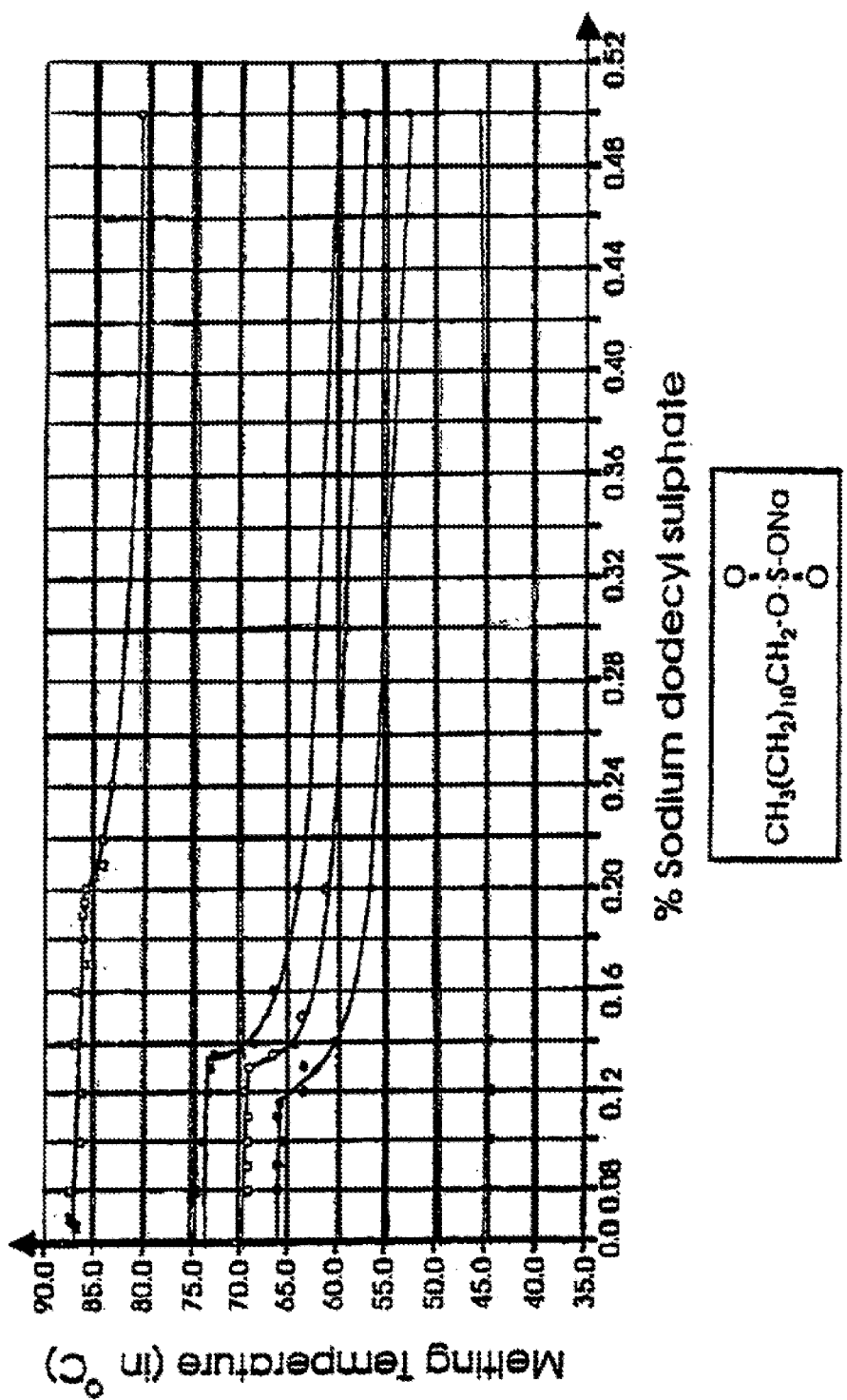
FIG. 1 shows the thermostability ($T_m$) of PNA/DNA-complexes dependent on the concentrations of SDS. It is clear that the thermostability of a DNA/DNA-hybrid is not dependent on the concentration of SDS, while, dependent on the degree of complementarity of the PNA and the DNA, the thermostability differs considerably. It further makes clear the optimal concentration of SDS for differentation in each case. The larger the distance between the $T_m$ values of the fully complementary and single base mismatched PNA/DNA duplex at a specific SDS concentration the better is the discrimination (selectivity of binding).

Legend to FIG. 1

Schematic representation of the thermostability of complementary PNA/DNA duplexes as a function of SDS in the hybridisation solution. Open squares: PNA (H-Ado$_3$-ACACGGAGGTGTAGAAAT-NH$_2$; 'Ado' designates an 8-amino-3,6-dioxa octanoic acid linker, SEQ.ID.NO. 1) hybridised to DNA (5'-ATTTCTACACCTCCGTGT-3', SEQ.ID.NO 2), Filled squares: PNA (H-Aha-TCGCGTTGT-TCGTGA-NH$_2$; 'Aha' designates an aminohexanoic acid linker, SEQ.ID.NO. 3) hybridised to DNA (5'-TCACGAA-CAACGCGA-3', SEQ.ID.NO. 4), Open circles: PNA (Ado$_3$-TGTACGTCACAACTA-Gly-NH$_2$, SEQ.ID.NO. 5) hybridised to DNA (5'-TAGTTGTGACGTACA-3', SEQ.ID.NO. 6), Filled circles: PNA (Ado$_3$-TGTACATCACAACTA-Gly-NH$_2$, SEQ.ID-NO. 9) hybridised to DNA (5'-TAGTTGT-GATGTACA-3', SEQ.ID.NO. 10), Filled triangles: DNA (5'-TGTACGTCACAACTA-3', SEQ.ID.NO. 7) hybridised to DNA (5'-TAGTTGTGACGTACA-3', SEQ. ID.NO. 6).

EXAMPLE 2

The Effect of SDS on PNA/DNA Duplexes is Reversible

To determine whether the observed SDS effect is reversible the following three situations were compared.
A. The PNA/DNA duplex is formed in the absence of SDS and SDS is added immediately prior to analyzes.
B. The PNA/DNA duplex is formed in the presence of SDS.
C. The PNA/DNA duplex is formed in the presence of SDS and diluted to low concentrations of SDS immediately prior to analysis.

The hybridisation reactions were made as follows.

| Situation A |
|---|
| Fully matched PNA/DNA (reaction 1): The hybridisation reaction (1 ml) contained 4.5 mM of a 15 mer PNA, 4.5 mM of a complementary DNA oligonucleotide and 25 mM $Na_2HPO_4$, pH 7.0. |
| Mismatched PNA/DNA (reaction 2): The hybridisation reaction (1 ml) contained 4.5 mM of a 15 mer PNA, 4.5 mM of a single base mismatched DNA oligonucleotide and 25 mM $Na_2HPO_4$, pH 7.0. |

The solutions were heated to 95° C. and left to form hybrids at room temperature over night. The following day 2 ml of 25 mM $Na_2HPO_4$, pH 7.0, 1.5% SDS was added to hybridisation reaction 1 (final concentration 25 mM $Na_2HPO_4$, pH 7.0, 1.0% SDS) and 2 ml of 25 mM $Na_2HPO_4$, pH 7.0, 0.15% SDS was added to hybridisation reaction 2 (final concentration 25 mM $Na_2HPO_4$, pH 7.0, 0.1% SDS). Immediately after addition of buffer the thermal stability of the PNA/DNA duplexes were determined spectrophotometrically using a Perkin-Elmer, λ2 spectrophotometer.

| Situation B |
|---|
| Fully matched PNA/DNA (reaction 3): The hybridisation reaction (300 m) contained 4.5 mM of a 15 mer PNA, 4.5 mM of a complementary DNA oligonucleotide and 25 mM $Na_2HPO_4$, pH 7.0, 1.0% SDS. |
| Fully matched PNA/DNA (reaction 4): The hybridisation reaction (1 ml) contained 4.5 mM of a 15 mer PNA, 4.5 mM of a complementary DNA oligonucleotide and 25 mM $Na_2HPO_4$, pH 7.0, 0.1% SDS. |
| Mismatched PNA/DNA (reaction 5): The hybridisation reaction (1 ml) contained 4.5 mM of a 15 mer PNA, 4.5 mM of a single base mismatched DNA oligonucleotide and 25 mM $Na_2HPO_4$, pH 7.0, 0.1% SDS. |

The solutions were heated to 95° C. and left to form hybrids at room temperature over night. The following day 2.7 ml of 25 mM $Na_2HPO_4$, pH 7, 1.0% SDS was added to reaction 3 (final concentration 25 mM $Na_2HPO_4$, pH 7.0, 1.0% SDS) and 2.0 ml of 25 mM $Na_2HPO_4$, pH 7.0, 0.1% SDS was added to reaction 4 and 5 (final concentration 25 mM $Na_2HPO_4$, pH 7.0, 0.1% SDS). Immediately after addition of buffer the thermal stability of the PNA/DNA duplexes were determined spectrophotometrically using a Perkin-Elmer, λ2 spectrophotometer.

| Situation C |
|---|
| Fully matched PNA/DNA (reaction 6): The hybridisation reaction (300 ml) contained 4.5 mM of a 15 mer PNA, 4.5 mM of a complementary DNA oligonucleotide and 25 mM $Na_2HPO_4$, pH 7.0, 1.0% SDS. |
| Mismatched PNA/DNA (reaction 7): The hybridisation reaction (300 ml) contained 4.5 mM of a 15 mer PNA, 4.5 mM of a single base mismatched DNA oligonucleotide and 25 mM $Na_2HPO_4$, pH 7.0, 1.0% SDS. |

The solutions were heated to 95° C. and left to form hybrids at room temperature over night. The following day 2.7 ml of 25 mM $Na_2HPO_4$, pH 7.0 was added to both hybridisation reactions 6 and 7 (final concentration 25 mM $Na_2HPO_4$, pH 7, 0.1% SDS). Immediately after addition of buffer the thermal stability of the PNA/DNA duplexes were determined spectrophotometrically using a Perkin-Elmer, λ2 spectrophotometer.

The results of the analyses are shown in table 1A (matched PNA/DNA duplex) and 1B (mismatched PNA/DNA duplex). As can be seen the $T_m$ of the PNA/DNA duplexes depend only on the final SDS concentration showing that the effect of SDS is reversible.

Legend to FIG. 2. A: Thermostability of a complementary PNA/DNA duplex (PNA:Ado$_3$-TGTACGTCACAACTA-Gly-NH$_2$ (SEQ.ID.NO. 5) and DNA:5'-TAGTTGTGACG-TACA-3', SEQ.ID.NO. 6) as a function of the order of SDS addition/dilution. B: Thermostability of a single base mismatched PNA/DNA duplex (PNA:Ado$_3$-TGTACGTCA-CAACTA-Gly-NH$_2$, SEQ.ID.NO. 5 and DNA:5'-TAGT-TGTCACGTACA-3', SEQ.ID.NO. 11) as a function of the order of SDS addition/dilution.

EXAMPLE 3

Figure 3:
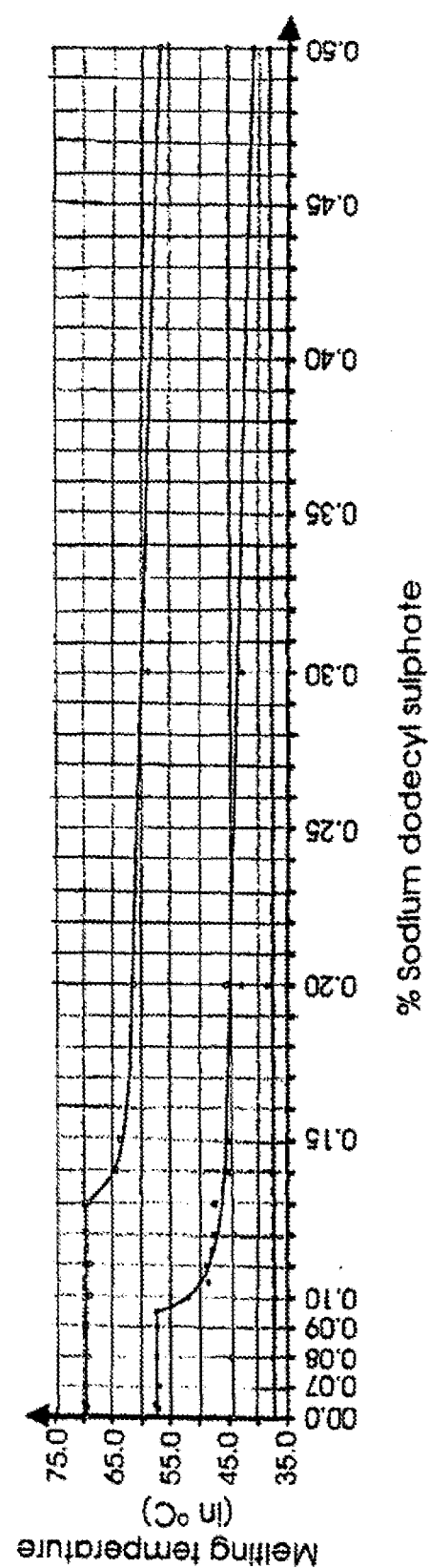
FIG. 3 shows the influence of a mismatch on the thermostability of PNA/DNA-complexes versus DNA/DNA-hybrids. It becomes clear that the specificity (difference between the $T_m$ of the fully complementary and single base mismatched PNA/DNA duplex) is higher for PNA-DNA-complexes at all SDS concentrations, but that this higher specificity can be even increased by choosing SDS above a certain concentration. The specificity is the highest, in this example, at concentrations between 0.95% SDS and 0.13% SDS, increasing from 0.95%. Even above 0.13% SDS the specificity is higher than below 0.95% SDS. While the concentration range may differ for different sequences and lengths, the general trend is visible.
Figure 4:
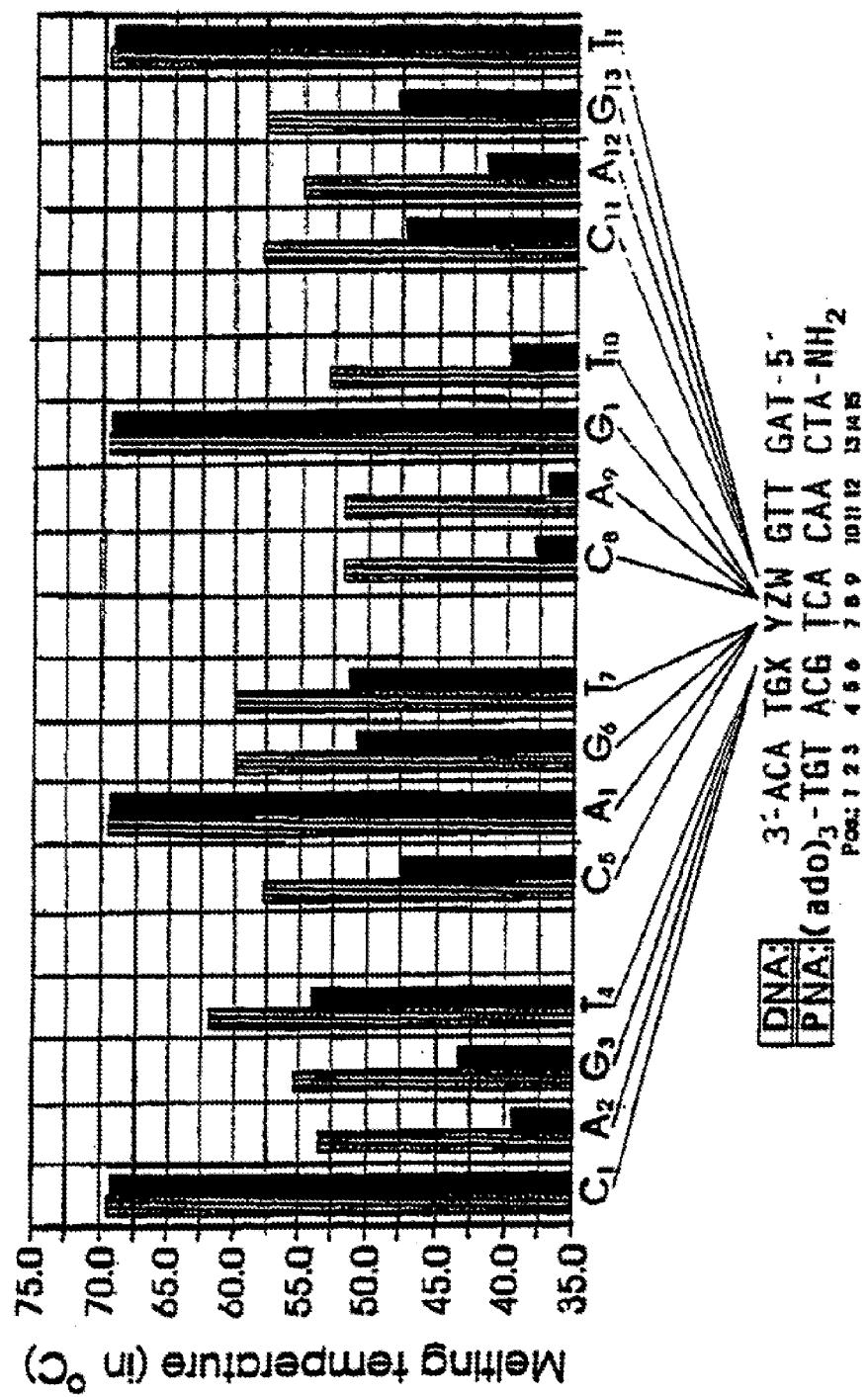
FIG. 4 shows the thermostability of PNA/DNA-complexes having different mismatches, in the absence of SDS and in the presence of the maximum concentration of SDS which does not affect the fully complementary PNA/DNA duplex.

SDS can be Used to Modulate the Specificity of PNA for its Complementary DNA A series of 1 ml hybridisation reactions were set up containing 25 mM Na$_2$HPO$_4$, pH 7.0, 4.5 mM of a 15mer PNA, 4.5 mM of either a complementary or a single base mismatched DNA oligonucleotide complementary DNA oligonucleotide and SDS from 0 to 0.5%. The solutions were heated to 95° C. and left to form PNA/DNA hybrids at room temperature over night. The following day additional 2 ml of the appropriate buffer (25 ml Na$_2$HPO$_4$, pH 7.0 and SDS from 0 to 0.5%) was added to the hybridisation solutions and the thermal stability, measured as melting temperature, T$_m$, were determined spectrophotometrically using a Perkin-Elmer, λ2 spectrophotometer. As a control a DNA hybridised to either its complementary DNA oligonucleotide or a DNA oligonucleotide containing a mismatch were analysed. As shown in FIG. 3, the T$_m$ values of neither the fully complementary DNA/DNA duplex nor the T$_m$ of the single base mismatched DNA/DNA duplex are affected by the presence of SDS in the concentration range tested (0 to 0.5%). In contrast, the T$_m$'s of both the fully complementary PNA/DNA duplex and the single base mismatched PNA/DNA duplex are affected by SDS. The concentrations of SDS required to affect the T$_m$'s of the two different PNA/DNA duplexes, however, is quite different. Thus, the PNA/DNA duplex that contained a mismatch is affected by SDS concentrations above 0.095% whereas the fully matched PNA/DNA duplex is not affected until the SDS concentration exceeded 0.13%. This result shows that SDS can be used to increase the specificity of PNA for its complementary DNA. The analysis was expanded to include the 12 possible different single base mismatches between a PNA and a DNA oligonucleotide. FIG. 4 shows a schematic comparison of the obtained T$_m$ values in the absence of SDS and in the presence of the highest SDS concentration that does not affect the fully complementary PNA/DNA duplex (0.13%). At this SDS concentration the thermal stability of all mismatched PNA/DNA duplexes are considerably affected having T$_m$'s between 15-32° C. compared to 7-17° C. in the absence of SDS. Hence, the ability of SDS to increase the specificity of PNA for its fully matched DNA target is a general phenomena.

Legend to FIG. 3: Schematic representation of the thermostability of complementary and single base mismatched PNA/DNA and DNA/DNA duplexes as a function of SDS in the hybridisation solution. Open squares: PNA (Ado$_3$-TG-TACGTCACAACTA-Gly-NH$_2$, SEQ. ID.NO. 5) hybridised to DNA (5'-TAGTTGTGACGTACA-3', SEQ.ID.NO. 6); Filled squares: PNA (Ado$_3$-TGTACGTCACAACTA-Gly-NH$_2$, SEQ.ID.NO. 5) hybridised to DNA (5'-TAGTTGC-GACGTACA-3', SEQ.ID.NO. 8), Open circles: DNA (5'-TGTACGTCACAACTA-3', SEQ.ID.NO. 7) hybridised to DNA (5'-TAGTTGTGACGTACA-3'; SEQ.ID.NO. 6), Filled circles: DNA (5'-TGTACGTCACAACTA-3', SEQ.ID.NO. 7) hybridised to DNA (5'-TAGTTGCGACGTACA-3', SEQ.ID.NO. 8).

Legend to FIG. 4: Schematic representation of the thermostability of a complementary and 12 single base mismatched PNA/DNA duplexes in the absence of SDS and at the highest concentration of SDS that did not affect the fully complementary PNA/DNA duplex. Grey bars: Thermostability of PNA/DNA duplexes in the absence of SDS. Black bars: Thermostability of PNA/DNA duplexes in the presence of 0.13% SDS.

EXAMPLE 4

Figure 5:
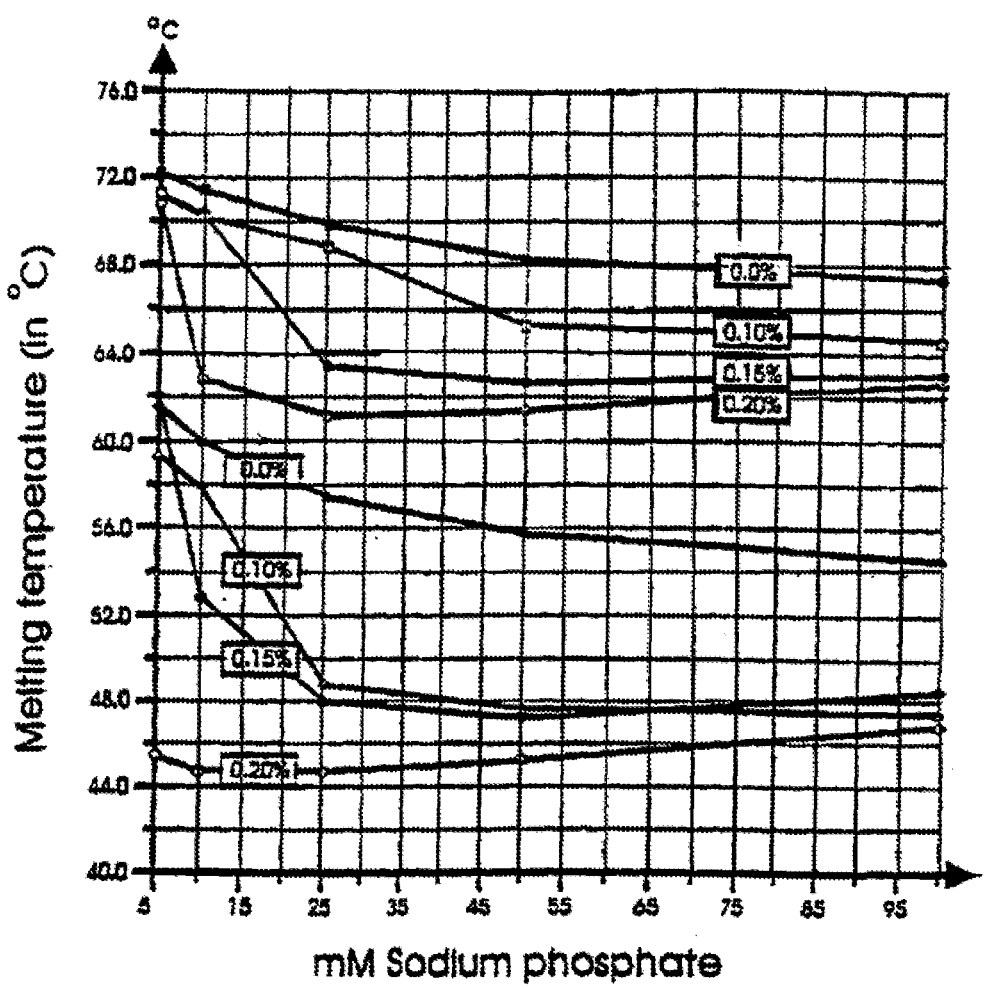
FIG. 5 shows the thermostability of PNA-DNA-complexes at different SDS-concentrations and different salt concentrations. The upper four curves are matching PNA/DNA-duplexes, the lower four curves are single mismatch PNA/DNA duplexes.

The Effect of SDS on PNA/DNA Duplexes can be Modulated by the Ionic Strength of the Hybridisation Solution A series of 1 ml hybridisation reactions were set up containing 4.5 mM of a 15mer PNA, 4.5 mM of either a complementary or a single base mismatched DNA oligonucleotide and varying concentrations of Na$_2$HPO$_4$, pH 7.0 and SDS. The solutions were heated to 95° C. and left to form hybrids at room temperature over night. The following day the samples were diluted to 3 ml without changing the concentration of Na$_2$HPO$_4$, pH 7.0 and SDS. Subsequently the thermal stability of each of the duplexes, measured as melting temperature, T$_m$, were determined spectrophotometrically using a Perkin-Elmer, λ2 spectrophotometer. As shown in FIG. 5, the level of SDS required to produce an effect on the T$_m$ of both the complementary and single base mismatched PNA/DNA duplexes varies with the ionic strength of the solution. Hence, as the ionic strength is lowered a higher concentration of SDS is required to produce a T$_m$ effect. This indicates that A: SDS does not exert its effect as SDS molecules per see but rather via a higher order SDS structure (i.e. micellar SDS) the formation of which is dependent on the ionic strength of the solution.

B: That SDS and ionic strength in combination can be used to modulate the ability of a PNA to discriminate between a fully matched vs. a single base mismatched DNA target.

Legend to FIG. 5: Schematic representation of the thermostability of complementary and single base mismatched PNA/DNA duplexes as a function of SDS and ionic strength of the hybridisation solution. The fully complementary. PNA/DNA duplex were made by hybridising the PNA (Ado$_3$-TGTACGTCACAACTA-Gly-NH$_2$, SEQ.ID.NO. 5) to DNA (5'-TAGTTGTGACGTACA-3', SEQ.ID.NO. 6). The single base mismatched PNA/DNA duplex was made by hybridising the PNA (Ado$_3$-TGTACGTCACAACTA-Gly-NH$_2$, SEQ.ID. NO. 5) to DNA (5'-TAGTTGCGACGTACA-3', SEQ.ID.NO. 8). Filled squares: fully matched duplex in the absence of SDS. Open squares: fully matched duplex in the presence of 0.10% SDS. Filled circles: fully matched duplex in the presence of 0.15% SDS. Open circles: fully matched duplex in the presence of 0.20% SDS. Filled triangles: single base mismatched duplex in the absence of SDS. Open triangles: single base mismatched duplex in the presence of 0.10% SDS. Filled diamonds: single base mismatched duplex in the presence of 0.15% SDS. Open diamonds: single base mismatched duplex in the presence of 0.20% SDS

EXAMPLE 5

Figure 6:
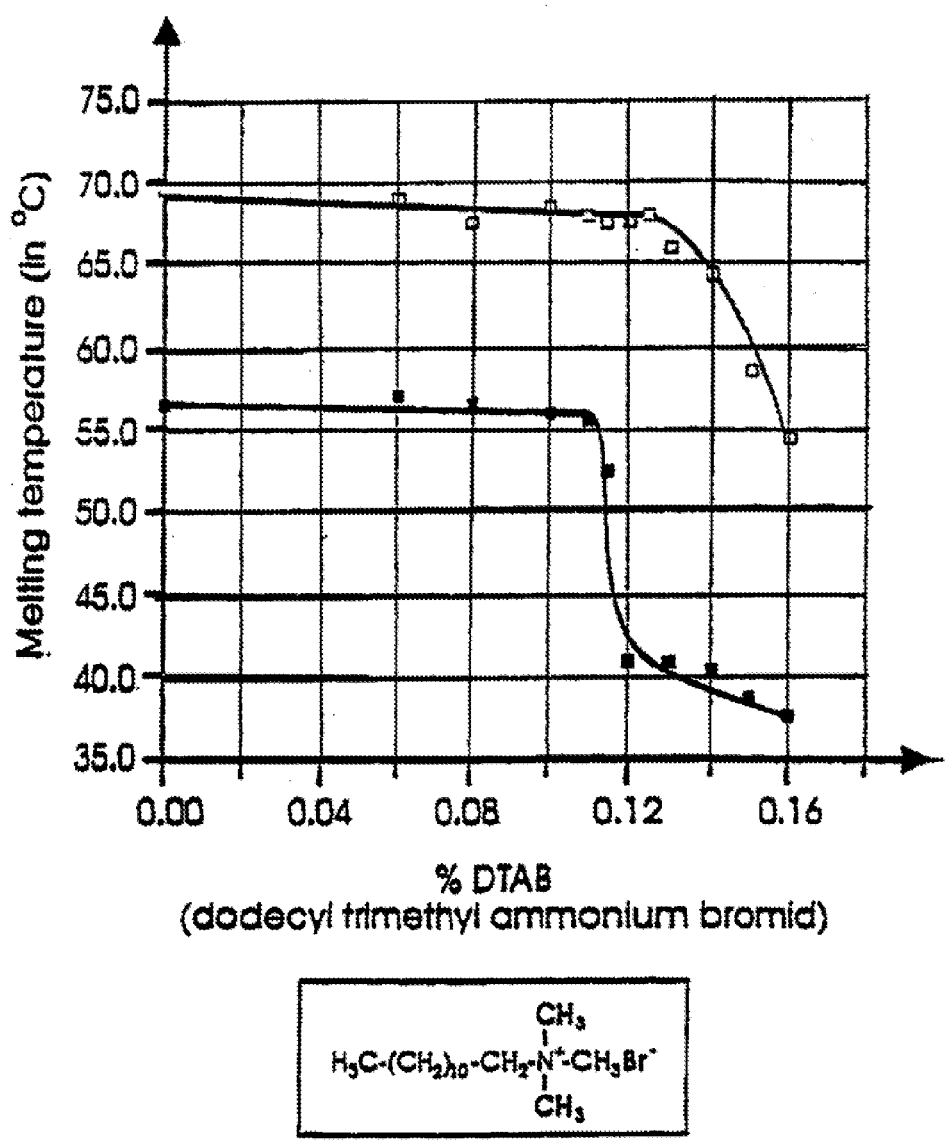
FIG. 6 shows the thermostability of a PNA/DNA-duplex versus a DNA/DNA-duplex at different concentrations of another detergent (DTAB).

In Addition to SDS, the Detergent DTAB can be Used to Modulate the Affinity and Specificity of PNA for its Complementary DNA A series of 1 ml hybridisation reactions were set up containing 25 mM $Na_2HPO_4$, pH 7.0, 4.5 mM of a 15mer PNA and 4.5 mM of either a complementary or a single base mismatched DNA oligonucleotide and DTAB from 0 to 0.16%. The solutions were heated to 95° C. and left to form PNA/DNA hybrids at room temperature over night. The following day additional 2 ml of the appropriate buffer (25 ml $Na_2HPO_4$, pH 7.0 and DTAB from 0 to 0.16%) was added to the hybridisation solutions and the thermal stability of each of the duplexes, measured as melting temperature, $T_m$, were determined spectrophotometrically using a Perkin-Elmer, λ2 spectrophotometer. As shown in FIG. 6, the $T_m$'s of both the fully complementary PNA/DNA duplex and the single base mismatched PNA/DNA duplex is affected by DTAB. The concentrations of DTAB required to affect the $T_m$'s of the two different PNA/DNA duplexes, however, are different. Thus, the PNA/DNA duplex that contained a mismatch is affected by DTAB concentrations above 0.11% whereas the fully matched PNA/DNA duplex is not affected until the DTAB concentration exceeded 0.125%. This result shows that DTAB, similar to SDS, can be used to modulate the affinity and specificity of PNA for its complementary DNA.

Legend to FIG. 6: Schematic representation of the thermostability of complementary and single base mismatched PNA/DNA and DNA/DNA duplexes as a function of DTAB in the hybridisation solution. Open squares: PNA ($Ado_3$-TGTACGTCACAACTA-Gly-$NH_2$, SEQ.ID.NO. 5) hybridised to DNA (5'-TAGTTGTGACGTACA-3', SEQ.ID.NO. 6); Filled squares: PNA ($Ado_3$-TGTACGTCACAACTA-Gly-$NH_2$, SEQ.ID.NO. 5) hybridised to DNA (5'-TAGTTGCGACGTACA-3', SEQ.ID.NO. 8)

EXAMPLE 6

The Detergent Lithium Dodecyl Sulphate (LiDS) can be Used to Modulate the Affinity and Specificity of PNA for its Complementary DNA A series of 1 ml hybridisation reactions were set up containing 25 mM $Na_2HPO_4$, pH 7.0, 4.5 µM of a 15mer PNA and either 4.5 µM of a complementary or single base mismatched DNA oligonucleotide and LiDS from 0 to 0.3%. The solutions were heated to 95° C. for 5 min and left to form hybrids at room temperature over night. The following day additional 2 ml of the appropriate buffer (25 mM $Na_2HPO_4$, pH 7.0 and LIDS from 0 to 0.3%) was added to the hybridisation solutions and the thermal stability of each of the duplexes (measured as melting temperature, $T_m$) were determined spectrophotometrically using a Perkin-Elmer λ-2 spectrophotometer. As shown in FIG. 5 the $T_m$ of the PNA/DNA duplex are both affected by the addition of LIDS ans similar to the effect of SDS in example 3, this effect occurs at lower LiDS concentrations for the single base mismatched PNA/DNA duplex than for the complementary PNA/DNA duplex. Compared to SDS, however, the effect of LIDS occurs at lower concentrations.

Figure 7:
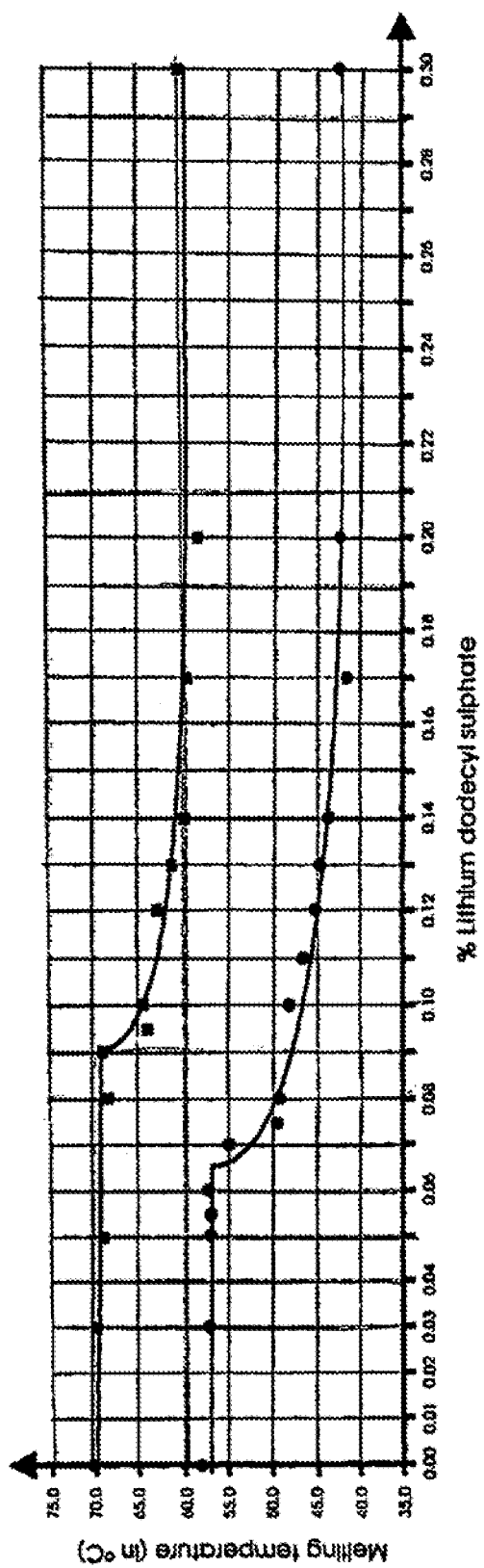
FIG. 7 shows that LiDS exercts an effect similar to SDS on PNA/DNA duplexes.

Legend to FIG. 7: Schematic representation of the thermostability of complementary and single base mismatched complexes of PNA/DNA and DNA/DNA as a function of the concentration of LiDS in the hybridisation solution. Squares: Fully complementary PNA/DNA duplex (PNA: $Ado_3$-TGTACGTCACAACTA-Gly-$NH_2$ (SEQ.ID.NO.5)) hybridised to DNA: 5'-TAGTTGTGACGTACA-3' (SEQ.ID.NO.6)), Circles: single base mismatched PNA/DNA duplex (PNA: $Ado_3$-TGTACGTCACAACTA-Gly-$NH_2$ (SEQ.ID.NO.5)) hybridised to DNA: 5'-TAGTTGCGACGTACA-3' (SEQ.ID.NO.8), location of mismatch is underlined).

EXAMPLE 7

Synthesis of PNA Oligomers

PNA synthesis is performed by conventional solid phase peptide synthesis following the Boc strategy. PNA oligomers can be synthesised manually, but automated synthesis is much more appropriate. We are currently synthesising the oligomers on a ABI 433A peptide synthesiser and the following description will be based on this and our standard 5 micromole scale. The PNA monomers used are: BocA(Z)—OH, Boc-C(Z)—OH, Boc-G(Z)—OH and Boc-T—OH (Boc=tert butyl oxycarbonyl for the backbone amino groups and the amino group of 8-amino-3,6-dioxa-octanoic acid (DE-A-3943522), glycine and 6-amino-hexanoic acid; Z=benzyloxy carbonyl for the bases' exocyclic amino groups).

Resin 50 mg of MBHA resin (loading ca. 0.100 mmol/g) is used in every synthesis. The resin is downloaded with the first monomer, amino acid, etc. in the appropriate sequence (the loading is checked by quantitative Kaiser test).

Preparation of Boc-Gly-Resin (or Boc-Monomer-Resin)

The experimental is illustrated for Boc-Gly-resin but Boc-monomer-resins are prepared analogously. 3 g MBHA resin (4-methyl-Benzhydrylamine 100-200 mesh, Nova Biochem) (ca. 0.45 mmol/g, 1.35 mmol amines) is swelled in DCM (dichloromethane, Labscan) and is then washed with DCM (2×), 5% DIEA (N,N-diisopropylethylamine, Aldrich) in DCM (3 min), DCM (2×).

Boc-Gly-OH (210 mg (1.20 mmol), MW: 175.4 g/mol) is dissolved in DMF/pyridine/DIEA (15/15/1) and HBTU (2-(1H-benzotriazole-1-yl)-1,1,3,3-tetra methyluronium hexafluorophosphate, Nova Biochem) (450 mg, 1.19 mmole) is similarly dissolved in DMF/pyridiine/DIEA. The HBTU is added to the amino acid and preactivated for 1 min. This mixture is then added to the resin. Use only the amount of solvent that is accurately necessary to cover the resin.

Let this react over night. Then the unreacted amino groups on the resin is capped with acetic anhydride/pyridine/NMP (N-methyl-pyrrolidone) (1/2/2) for 2-3 h. The Kaiser test must now be negative.

The same amounts, solvents and times are used for loading PNA monomers.

| Kaiser Tests | |
| --- | --- |
| Reagent A: | Mix 40 g phenol with 10 ml ethanol. Warm until dissolved. Dissolve 65 mg potassium cyanide in 100 ml water. Dilute |

| | Kaiser Tests |
|---|---|
| | 2 ml of the KCN solution to 100 ml pyridine. Mix the phenol and KCN/pyridine solutions. |
| Reagent B: | Dissolve 2.5 g of ninhydnn in 50 ml ethanol. |

Kaiser Test (Qualitive)

Take out about 2-5 mg suction dried resin and add 1 drop of A and 2 drops of B. Heat to 100° C. for 2 min (Blue (or black) positive; light yellow: negative).

Kaiser Test (Quantitive)

Weigh out ca. 50 mg of down loaded (+capped) resin and deprotects with TFA(trifluoroacetic acid)/m-cresol 2×3 min. Wash the resin (+DIEA treatment). The resin is at least washed with DCM which is dried of by suction. Take samples out 5-10 mg and place these in tarred tubes.

Heat these on the heat block for 10 min. Determine the "dry" mass of the resin ($W_{mg}$). Add 100 μl reagent A and 25 μl reagent B to each tube. Heat for 5 min at 100° C. Add 1 ml 60% alcohol and filter the resin off. Wash the resin 2 times with 0.2 ml of 0.5 M $Et_4NCl$ in DCM. Adjust the total volume to 2 ml by adding 475 ml 60% ethanol (=$V_{ml}$). Measure the absorbance at 570 nm with 60% ethanol as reference. If the absorbency is higher than 2.5 dilute with 60% ethanol (NB: $V_{ml}$ will be changed). Calculate the mean value of the tests by the following equation:

$$\mu mole(NH_2)/g\ resin = \frac{100 \times A_{570} \times V_{ml}}{1.5 \times W_{mg}}$$

Values around 0.050 to 0.100 are ideally.

Lower values give less product higher values might give aggregation problems during oligomerization (Ref: Anal. Biochem. 117, 147-157 (1981)).

Boc-Deprotection

The boc-protecting groups are removed by adding 1 ml of TFA/m-Cresol (95/5) for one time 1 min and one time 3.5 min.

Coupling

100 μl (026M) of each monomer is placed in separate cartridges. The synthesiser will use this amount of monomer in each coupling. Before each coupling first 125 μl HBTU (0.201 M) and then 125 μl DIEA (0.41M) is added to the monomer solution in the cartridge. The solvent in these solutions is NMP. A total of 350 μl is added to the reaction vessel. The coupling is performed in 33 mm.

Capping

Following the coupling the last added monomer is capped. This is done by adding 1 ml of $Ac_2O$/NMP/Pyridine (1/2/2) in 1 min to the reaction vessel.

Cleavage from Resin

After the last monomer is coupled the oligomer is removed from the resin by treatment of TFMSA (trifluoromethane sulphonic acid). This procedure yields an oligomer having its carboxyl end modified as an amide (nominated —$NH_2$-end, while the amino end is nominated —H).

All solutions must be freshly prepared each time

1. Prepare Two Solutions:
   I: TFA/Dimethylsulphide/m-Cresol (1:3:1)
   II: TFA/TFMSA(Trifluoromethylsulphonic acid, 9:1)

Wash the resin with 100% TFA in 1 min. Add 1 mol of solution I and thereafter 1 ml of solution II to the reaction vessel (glass vessel with screw cap and fritte) and let in stir for 1 h. Wash with 100% TFA in 1 min. Prepare a solution of TFMSA/TFA/m-Cresol (2:8:1) and add 2 ml of this to the reaction vessel. The colour of the resin turns black! Let that stir for 1.5 h. The black solution is "blown out" in ether (25-50 ml) to precipitate the oligomer. Wash the black resin 2 times with 1-2 ml of TFA and add also this to the ether. Filter the precipitate with a 0.44μ Teflon™ filter and wash several times with ether. Remove the oligo from the filter by dissolving it in 5% acetic acid in water and suck this through the filter. Wash several times. Freeze the aqueous solution of the oligomer and remove the solvent by freeze drying.

QC-Check

Based on HPLC the crude material is normally obtained with 80-90% purity (15 mers). This is purified by reverse phase HPLC. A Delta pak ($C_{1-8}$), 100 Å, 5 μm, 3.9×150 (Waters) (flow 1 ml/min) column is used for the analytical analysis and a Vydac ($C_{18}$), 300 Å, 5 μm, 10×250 (flow 3 mml/min) is used for preparative purposes.

The gradient used in both cases is 0-2 min 100% A; 2-30 min 100-60% A; 30-35 min 60% A; 35-40 min 60-0% A; 40-45 min 0% A, 45-50 min 0-100% A; 50-55 min 100% A.

(A: 0.1% TFA in water, B: 0.1% TFA in acetonitrile).

The pure material is characterised by MALDI-TOF mass spectrometry and the thermal stability ($T_m$) on the PNA oligomer against the complementary DNS target is assessed.

The exact amount of PNA in a sample is measured by the optical density of the solution.

The following values are uses:

$\epsilon_0$:T=8.8, C=7.3, G=11.7, A=15.4 OD=$\epsilon_0 \times \mu g \times Mw^1$

The invention claimed is:

1. A method for specifically determining the presence of at least one single stranded target nucleic acid in the presence of at least one other nucleic acid sequence, comprising contacting a target nucleic acid with a probe which binds to said target nucleic acid to form a complex between said target nucleic acid and probe and, after formation of the complex in a reaction mixture, adding to the reaction mixture a compound which enhances the specificity of binding, thereby contacting said complex with the compound which enhances the specificity of binding, wherein said target nucleic acid, said probe or both said target nucleic acid and said probe are peptide nucleic acid binding partners and wherein said complex is in a solution when contacted with said compound.

2. The method according to claim 1, wherein said compound is soluble in aqueous solutions.

3. The method according to claim 1, wherein said compound has a hydrophobic part or both a hydrophobic part and a hydrophilic part.

4. The method according to claim 1, wherein said compound is a surfactant or detergent.

5. The method according to claim 4, wherein said compound is sodium dodecyl sulphate.

6. The method according to claim 1, wherein said compound is positively charged.

7. The method according to claim 1, wherein said target nucleic acid and probe or said complex is contacted with said compound in a solution containing salts at a concentration between 5 to 50 mM.

8. The method according to claim 1, wherein the compound is present in a concentration of between 0.05 and 0.5% w/v.

9. A method for lowering the assay temperature for the specific binding of a nucleic acid to a peptide nucleic acid binding partner in a reaction mixture, comprising adding a compound selected from the group consisting of surfactants and detergents to the reaction mixture in an amount effective to lower the assay temperature for the specific binding of a single stranded target nucleic acid to the peptide nucleic acid binding partner, wherein the compound is added to the reaction mixture after formation of a complex between the nucleic acid and the peptide nucleic acid binding partner.

10. The method according to claim 1, wherein said peptide nucleic acid binding partners have the general formula 1:

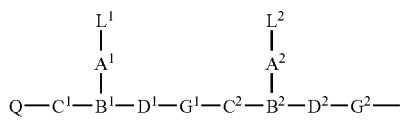

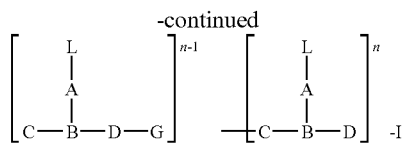

wherein
n is at least 2,
each of $L^1$-$L^n$ is independently selected from the group consisting of hydrogen, hydroxy, ($C_1$-$C_4$) alkanoyl, naturally occurring nucleobases, non-naturally occurring nucleobases, aromatic moieties, DNA intercalators, nucleobase-binding groups, heterocyclic moieties, reporter ligands and chelating moieties;

each of $C^1$-$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, ($C_1$-$C_4$)aralkyl, heteroaryl, hydroxy, ($C_1$-$C_6$)alkoxy, ($C_1$-$C_6$)alkylthio, $NR^3R^4$ and $SR^5$, where $R^3$ and $R^4$ are as defined below, and $R^5$ is hydrogen, ($C_1$-$C_6$)alkyl, hydroxy, ($C_1$-$C_4$) alkoxy, or ($C_1$-$C_4$) alkylthio-substituted($C_1$ to $C_6$)alkyl or $R^6$ and $R^7$ taken together complete an alicyclic or heterocyclic system;

each of $D^1$-$D^n$ is $(CR^6R^7)$, where $R^6$ and $R^7$ are as defined above;

each of y and z is zero or an integer from 1 to 10, the sum y+z being at least 2, but not more than 10;

each of $G^1$-$G^{n-1}$ is $NR^3CO$—, —$NR^3C^5$—, $NR^3SO$— or $NR^3SO^2$—, where $R^3$ is as defined below;

each of $A^1$-$A^n$ and $B^1$-$B^n$ are selected such that:

(a) A is a group of formula (IIa), (IIb), (IIc) or (IId), and B is N or $R^3N+$; or (b) A is a group of formula (IId) and B is CH;

Formula IIa

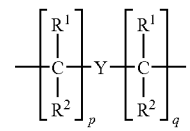

Formula IIb

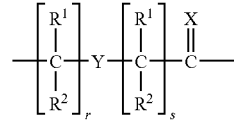

Formula IIc $$-\left[\begin{array}{c}R^1\\|\\C\\|\\R^2\end{array}\right]_r -Y-\left[\begin{array}{c}R^1\\|\\C\\|\\R^2\end{array}\right]_s -\overset{R^3}{\underset{|}{N}}-\overset{O}{\underset{\|}{C}}-$$

Formula IId $$-\left[\begin{array}{c}R^1\\|\\C\\|\\R^2\end{array}\right]_r -Y-\left[\begin{array}{c}R^1\\|\\C\\|\\R^2\end{array}\right]_s -\overset{X}{\underset{\|}{C}}-\overset{R^3}{\underset{|}{N}}-$$

wherein;

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or $(C_1-C_4)$alkoxy- or $(C_1-C_4)$ alkylthio-substituted, hydroxy, $(C_1-C_4)$ alkoxy, $(C_1-C_4)$alkylthio, amino and halogen; and each $R^3$ and $R^4$ is independently selected from the group consisting of hydrogen, $(C_1-C_4)$alkyl, hydroxy- or $(C_1-C_4)$ alkoxy- or $(C_1-C_4)$ alkylthio-substituted, $(C_1-C_4)$alkyl, hydroxy, $(C_1-C_4)$ alkoxy, $(C_1-C_4)$alkylthio and amino; and Q is $CO_2H$, —CONR'R", —$SO_3H$ or —$SO_2$—NR'R" or an activated derivative of —$CO_2H$ or —$SO_3H$, and I is —NR'R" wherein R' and R" are independently selected from the group consisting of hydrogen, $(C_1-C_4)$ alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers.

11. The method according to claim 9, wherein said peptide nucleic acid binding partners have the general formula 1:

$$Q-C^1-B^1-D^1-G^1-C^2-B^2-D^2-G^2-\left[\begin{array}{c}L\\|\\A\\|\\C-B-D-G\end{array}\right]_{n-1}-\left[\begin{array}{c}L\\|\\A\\|\\C-B-D\end{array}\right]_n -I$$

with $L^1$, $A^1$ above $C^1$ and $L^2$, $A^2$ above $C^2$ wherein n is at least 2, each of $L^1-L^n$ is independently selected from the group consisting of hydrogen, hydroxy, $(C_1-C_4)$ alkanoyl, naturally occurring nucleobases, non-naturally occurring nucleobases, aromatic moieties, DNA intercalators, nucleobase-binding groups, heterocyclic moieties, reporter ligands and chelating moieties;

each of $C^1-C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, $(C_1-C_4)$aralkyl, heteroaryl, hydroxy, $(C_1-C_6)$alkoxy, $(C_1-C_6)$alkylthio, $NR^3R^4$ and $SR^5$, where $R^3$ and $R^4$ are as defined below, and $R^5$ is hydrogen, $(C_1-C_6)$alkyl, hydroxy, $(C_1-C_4)$ alkoxy, or $(C_1-C_4)$ alkylthio-substituted$(C_1$ to $C_6)$alkyl or $R^6$ and $R^7$ taken together complete an alicyclic or heterocyclic system;

each of $D^1-D^n$ is $(CR^6R^7)_z$ where $R^6$ and $R^7$ are as defined above;

each of y and z is zero or an integer from 1 to 10, the sum y+z being at least 2, but not more than 10;

each of $G^1-G^{n-1}$ is $NR^3CO$—, —$NR^3C^5$, $NR^3SO$— or $NR^3SO^2$—, where $R^3$ is as defined below;

each of $A^1-A^n$ and $B^1-B^n$ are selected such that:

(a) A is a group of formula (IIa), (IIb), (IIc) or (IId), and B is N or $R^3N+$; or (b) A is a group of formula (IId) and B is CH;

Formula IIa $$-\left[\begin{array}{c}R^1\\|\\C\\|\\R^2\end{array}\right]_p -Y-\left[\begin{array}{c}R^1\\|\\C\\|\\R^2\end{array}\right]_q -$$

Formula IIb $$-\left[\begin{array}{c}R^1\\|\\C\\|\\R^2\end{array}\right]_r -Y-\left[\begin{array}{c}R^1\\|\\C\\|\\R^2\end{array}\right]_s -\overset{X}{\underset{\|}{C}}-$$

Formula IIc $$-\left[\begin{array}{c}R^1\\|\\C\\|\\R^2\end{array}\right]_r -Y-\left[\begin{array}{c}R^1\\|\\C\\|\\R^2\end{array}\right]_s -\overset{R^3}{\underset{|}{N}}-\overset{O}{\underset{\|}{C}}-$$

Formula IId $$-\left[\begin{array}{c}R^1\\|\\C\\|\\R^2\end{array}\right]_r -Y-\left[\begin{array}{c}R^1\\|\\C\\|\\R^2\end{array}\right]_s -\overset{X}{\underset{\|}{C}}-\overset{R^3}{\underset{|}{N}}-$$

wherein;

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or $(C_1-C_4)$alkoxy- or $(C_1-C_4)$ alkylthio-substituted, hydroxy, $(C_1-C_4)$ alkoxy, $(C_1-C_4)$alkylthio, amino and halogen; and each $R^3$ and $R^4$ is independently selected from the group consisting of hydrogen, $(C_1-C_4)$alkyl, hydroxy- or $(C_1-C_4)$ alkoxy- or $(C_1-C_4)$ alkylthio-substituted, $(C_1-C_4)$alkyl, hydroxy, $(C_1-C_4)$ alkoxy, $(C_1-C_4)$alkylthio and amino; and Q is $CO_2H$, —CONR'R", —$SO_3H$ or —$SO_2$—NR'R" or an activated derivative of —$CO_2H$ or —$SO_3H$, and I is —NR'R" wherein R' and R" are independently selected from the group consisting of hydrogen, $(C_1-C_4)$ alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<221> NAME/KEY: misc_structure
<222> LOCATION: (1)..(18)
<223> OTHER INFORMATION: PNA
<220> FEATURE:
<221> NAME/KEY: modified_base
```

```
<222> LOCATION: (1)
<223> OTHER INFORMATION: (8-Amino-3,6-dioxa octanoic acid linker) - 3
<220> FEATURE:
<223> OTHER INFORMATION: Description of Artificial Sequence: Non-natural
      Nucleic Acid Binding Partners

<400> SEQUENCE: 1
acacggaggt gtagaaat                                                        18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 2
atttctacac ctccgtgt                                                        18

<210> SEQ ID NO 3
<211> LENGTH: 15
<212> TYPE: DNA
<213> ORGANISM: Artificial Sequence
<220> FEATURE:
<221> NAME/KEY: misc_structure
<222> LOCATION: (1)..(15)
<223> OTHER INFORMATION: PNA
<220> FEATURE:
<221> NAME/KEY: modified_base
<222> LOCATION: (1)
<223> OTHER INFORMATION: Aminohexanoic Acid linker
<220> FEATURE:
<223> OTHER INFORMATION: Description of Artificial Sequence: Non-natural
      Nucleic Acid Binding Partners

<400> SEQUENCE: 3
tcgcgttgtt cgtga                                                           15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 4
tcacgaacaa cgcga                                                           15

<210> SEQ ID NO 5
<211> LENGTH: 15
<212> TYPE: DNA
<213> ORGANISM: Artificial Sequence
<220> FEATURE:
<221> NAME/KEY: misc_structure
<222> LOCATION: (1)..(15)
<223> OTHER INFORMATION: PNA
<220> FEATURE:
<221> NAME/KEY: modified_base
<222> LOCATION: (1)
<223> OTHER INFORMATION: (8-Amino-3,6-dioxa octanoic acid linker) - 3
<220> FEATURE:
<221> NAME/KEY: modified_base
<222> LOCATION: (15)
<223> OTHER INFORMATION: Gly-NH2
<220> FEATURE:
<223> OTHER INFORMATION: Description of Artificial Sequence: Non-natural
      Nucleic Acid Binding Partners

<400> SEQUENCE: 5
```

-continued tgtacgtcac aacta                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 6
tagttgtgac gtaca                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 7
tgtacgtcac aacta                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 8
tagttgcgac gtaca                                                    15

<210> SEQ ID NO 9
<211> LENGTH: 15
<212> TYPE: DNA
<213> ORGANISM: Artificial Sequence
<220> FEATURE:
<221> NAME/KEY: misc_structure
<222> LOCATION: (1)..(15)
<223> OTHER INFORMATION: PNA
<220> FEATURE:
<221> NAME/KEY: modified_base
<222> LOCATION: (1)
<223> OTHER INFORMATION: (8-Amino-3,6-dioxa octanoic acid linker) - 3
<220> FEATURE:
<221> NAME/KEY: modified_base
<222> LOCATION: (15)
<223> OTHER INFORMATION: Gly-NH2
<220> FEATURE:
<223> OTHER INFORMATION: Description of Artificial Sequence: Non-natural
      Nucleic Acid Binding Partners

<400> SEQUENCE: 9
tgtacatcac aacta                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 10
tagttgtgat gtaca                                                    15

```
<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Non-natural
      Nucleic Acid Binding Partners

<400> SEQUENCE: 11
tagttgtcac gtaca                                                  15
```